(12) United States Patent
Bhullar et al.

(10) Patent No.: US 7,510,643 B2
(45) Date of Patent: *Mar. 31, 2009

(54) SENSOR SYSTEM

(75) Inventors: Raghbir Singh Bhullar, Indianapolis, IN (US); Michael Lee Brown, Greenwood, IN (US); Vladimir B. Svetnik, Morristown, NJ (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 937 days.

This patent is subject to a terminal disclaimer.

(21) Appl. No.: 10/887,191

(22) Filed: Jul. 8, 2004

(65) Prior Publication Data

US 2004/0238357 A1    Dec. 2, 2004

Related U.S. Application Data

(62) Division of application No. 09/471,570, filed on Dec. 23, 1999, now Pat. No. 6,780,296.

(51) Int. Cl.
G01N 27/327    (2006.01)
(52) U.S. Cl. .................. 205/777.5; 204/403.04
(58) Field of Classification Search ............ 204/403.01, 204/403.04, 403.14, 400, 408; 205/777.5, 205/792
See application file for complete search history.

(56) References Cited

U.S. PATENT DOCUMENTS

| 4,062,750 | A |   | 12/1977 | Butler |              |
|-----------|---|---|---------|--------|--------------|
| 4,464,552 | A |   | 8/1984  | Pawlowski |           |
| 4,717,018 | A |   | 1/1988  | Sacherer et al. |     |
| 4,894,137 | A | * | 1/1990  | Takizawa et al. | 204/403.09 |
| 5,232,667 | A | * | 8/1993  | Hieb et al. | 422/82.04 |
| 5,264,103 | A | * | 11/1993 | Yoshioka et al. | 205/778 |
| 5,284,568 | A | * | 2/1994  | Pace et al. | 204/403.03 |
| 5,342,498 | A |   | 8/1994  | Graves et al. |       |
| 5,405,511 | A |   | 4/1995  | White et al. |        |
| 5,431,806 | A |   | 7/1995  | Suzuki et al. |       |
| 5,505,308 | A |   | 4/1996  | Eikmeier et al. |     |
| 5,554,531 | A |   | 9/1996  | Zweig |               |
| 5,762,770 | A | * | 6/1998  | Pritchard et al. | 204/403.14 |
| 5,972,715 | A |   | 10/1999 | Celentano et al. |    |

(Continued)

FOREIGN PATENT DOCUMENTS

EP    0 851 229 A1    12/1997

(Continued)

OTHER PUBLICATIONS

Thermal Conductivity of some common Materials, from the Engineering Toolbox website, 03/26/2008.*

(Continued)

Primary Examiner—Kaj K Olsen
(74) Attorney, Agent, or Firm—Brinks Hofer Gilson & Lione

(57) ABSTRACT

A sensor strip comprises an electrode substrate, an electrode set, on the electrode substrate, and a heat conducting layer, on the electrode substrate opposite the electrode set. A sensor instrument for use with this sensor strip comprises a temperature sensor, at a side of a gap for accepting the sensor strip, opposite electrical contacts. The invention provides an accurate determination of the temperature of a sample.

19 Claims, 3 Drawing Sheets

U.S. PATENT DOCUMENTS 6,046,051 A * 4/2000 Jina .......................... 436/69

FOREIGN PATENT DOCUMENTS

| EP | 0 878 713 A2 | 4/1998 |
| --- | --- | --- |
| JP | 08154903 | 6/1996 |
| WO | WO 95/14962 | 6/1995 |
| WO | WO 98/55856 | 12/1998 |
| WO | WO 99/30152 | 6/1999 |

OTHER PUBLICATIONS

Metals Handbook, Desk Edition (2nd), 1998. p. 115.

* cited by examiner

SENSOR SYSTEM

The present patent document is a divisional of Application Ser. No. 09/471,570, filed Dec. 23, 1999, now U.S. Pat. No. 6,780,296, incorporated by reference herein.

BACKGROUND OF THE INVENTION

The present invention relates to a thermally conductive electrochemical sensor.

Electrochemical biosensors are well known. They have been used to determine the concentration of various analytes from biological samples, particularly from blood. Electrochemical biosensors are described in U.S. Pat. Nos. 5,413,690; 5,762,770 and 5,798,031; as well as in International Publication No. WO99/13101, each of which are hereby incorporated by reference.

An electrochemical biosensor typically includes a sensor strip and a sensor instrument. The sensor strip includes a space that holds the sample to be analyzed, may include reagents to be released into the sample, and includes an electrode set. The electrode set normally includes an insulating substrate, and electrodes that contact the sample, which have contact pads for electrically connecting the electrodes to the sensor instrument.

The temperature of the sample during analysis will effect the signal detected by the electrochemical biosensor. In order to compensate for variations in sample temperature, most electrochemical biosensors measure the ambient temperature, typically by using a temperature sensor in the sensor instrument, and contain electronics for electrochemical analysis. The temperature of the actual sample may vary from the ambient temperature, depending on the humidity and local air movements, by three degrees, or more. Furthermore, the ambient temperature is not necessarily stable, and therefore algorithms have been used to compensate for changes in ambient temperature (see, for example, U.S. Pat. No. 5,405,511, hereby incorporated by reference). In addition, if the instrument is held in the hand during use, the recorded ambient temperature may be effected by the temperature of the hand.

None of these devices actually measures the temperature of the sample, but rather simply use the ambient temperature measurements to indirectly determine the temperature of at the sample site, or the temperature close to the sample. It would be desirable to more accurately measure the temperature of the sample, thus avoiding the need for compensatory algorithms, and improving measurement accuracy.

SUMMARY OF THE INVENTION

In one aspect, the invention is a sensor strip, comprising (a) an electrode substrate, (b) an electrode set, on the electrode substrate, and (c) a heat conducting layer, on the electrode substrate opposite the electrode set.

In another aspect, the invention is a sensor strip, comprising (a) an electrode substrate, and (b) an electrode set, on the electrode substrate, where the sensor strip has a thermal conductivity of at least 10 W/m-K.

In yet another aspect, the invention is a sensor instrument for accepting a sensor strip, comprising a gap, electrical contacts at a first side of said gap, and a temperature sensor, at a second side of the gap, opposite the electrical contacts.

In still another aspect, the invention is a method of making a sensor strip, comprising forming an electrode set on an electrode substrate; and attaching the electrode set to a heat conducing layer.

An advantage of the present invention is that it allows for accurate temperature measurement of the sensing region and sample.

As used herein, the phrase "electrode set" is a set of at least two electrodes, for example 2 to 60, or 3 to 20, electrodes. These electrodes may be, for example, a working electrode, a counter electrode, and a reference electrode.

Other features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
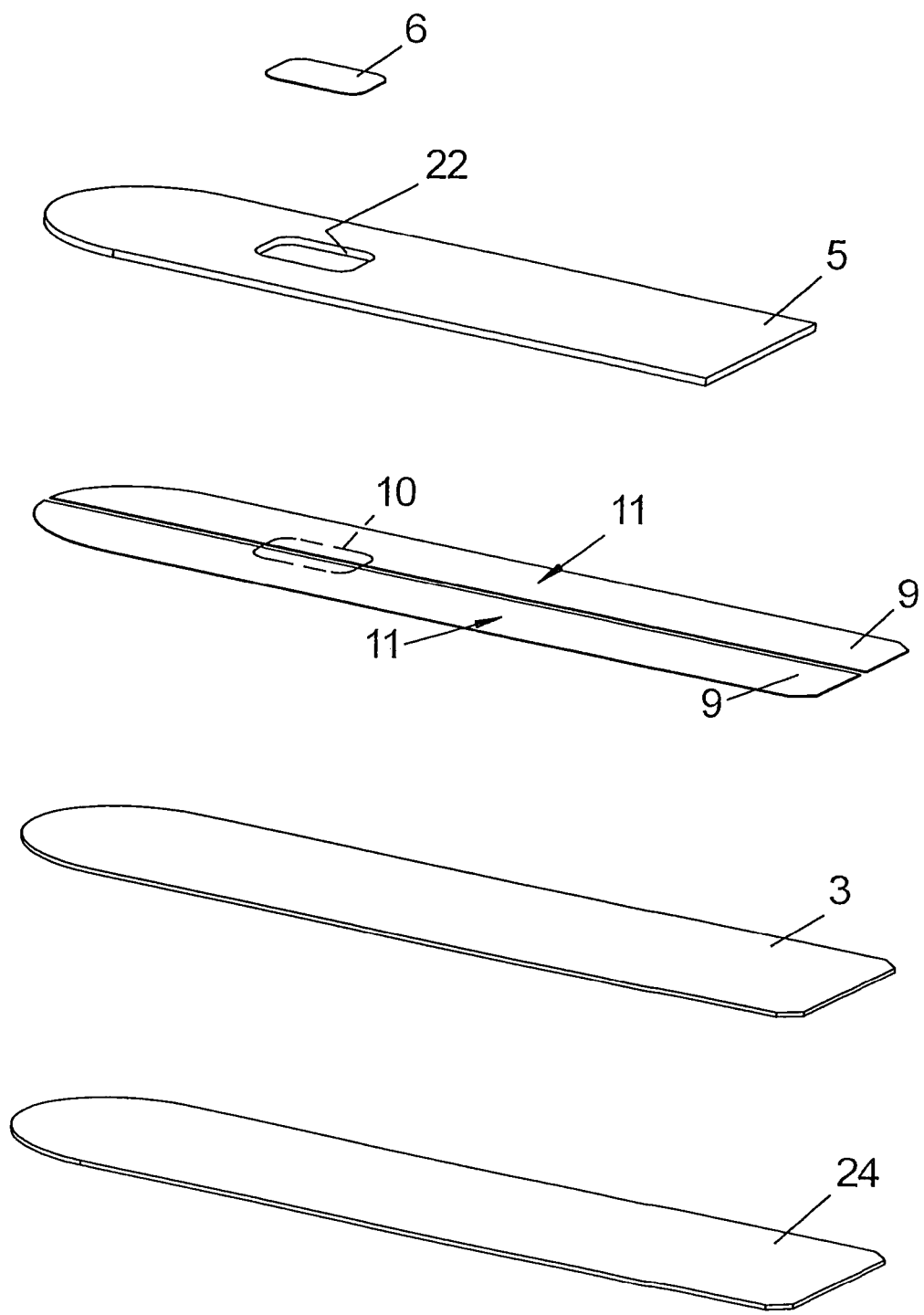
FIG. 1 is an exploded view of an embodiment of a sensor strip of the invention.
Figure 2:
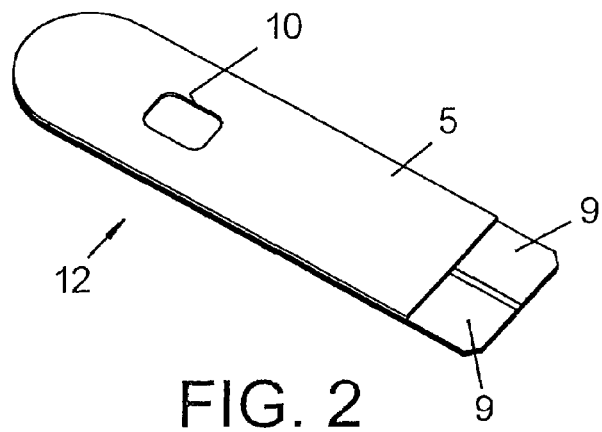
FIG. 2 is a top view of an embodiment of a sensor strip of the invention.
Figure 3:
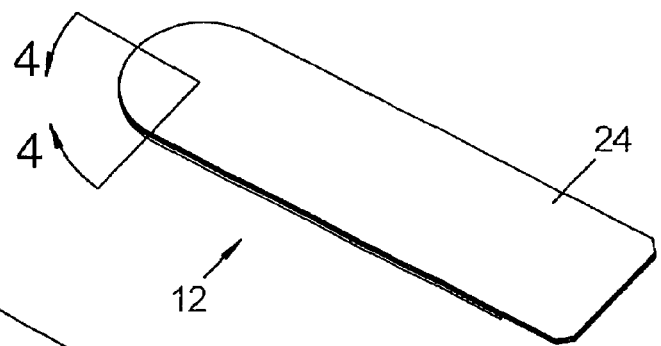
FIG. 3 is a bottom view of an embodiment of a sensor strip of the invention.

FIG. 2 is a top view of an embodiment of a sensor strip 12, FIG. 3 is a bottom view, and FIG. 1 is an exploded view. Illustrated in FIG. 1, are an electrode substrate 3, the contact pads 9 and 9, and sensing region 10, all of which are part of the electrodes 11 and 11. The electrodes are, in part, covered with a dielectric 5 exposing the sensing region 10, through hole 22 in the dielectric, and the contact pads 9 and 9. Reagent 6 is on the sensing region 10. Also illustrated is heat conducting layer 24 under the electrode substrate 3, which is most clearly illustrated in FIG. 3. In this embodiment, the sample is loaded from the top of the sensor strip via hole 22.

Figure 4:
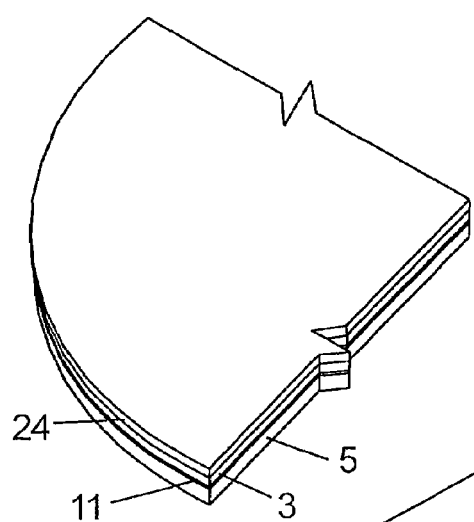
FIG. 4 is a detailed illustration of a side view, from the bottom, of a portion of the sensor strip shown in FIG. 3.

FIG. 4 provides a detailed illustration of a side view, from the bottom, of a portion the sensor strip 12. In this embodiment, the heat conducting layer 24 is in contact with the electrode substrate 3, which in turn is in contact with the electrodes 11. The electrodes are covered (in part) with dielectric 5.

Figure 5:
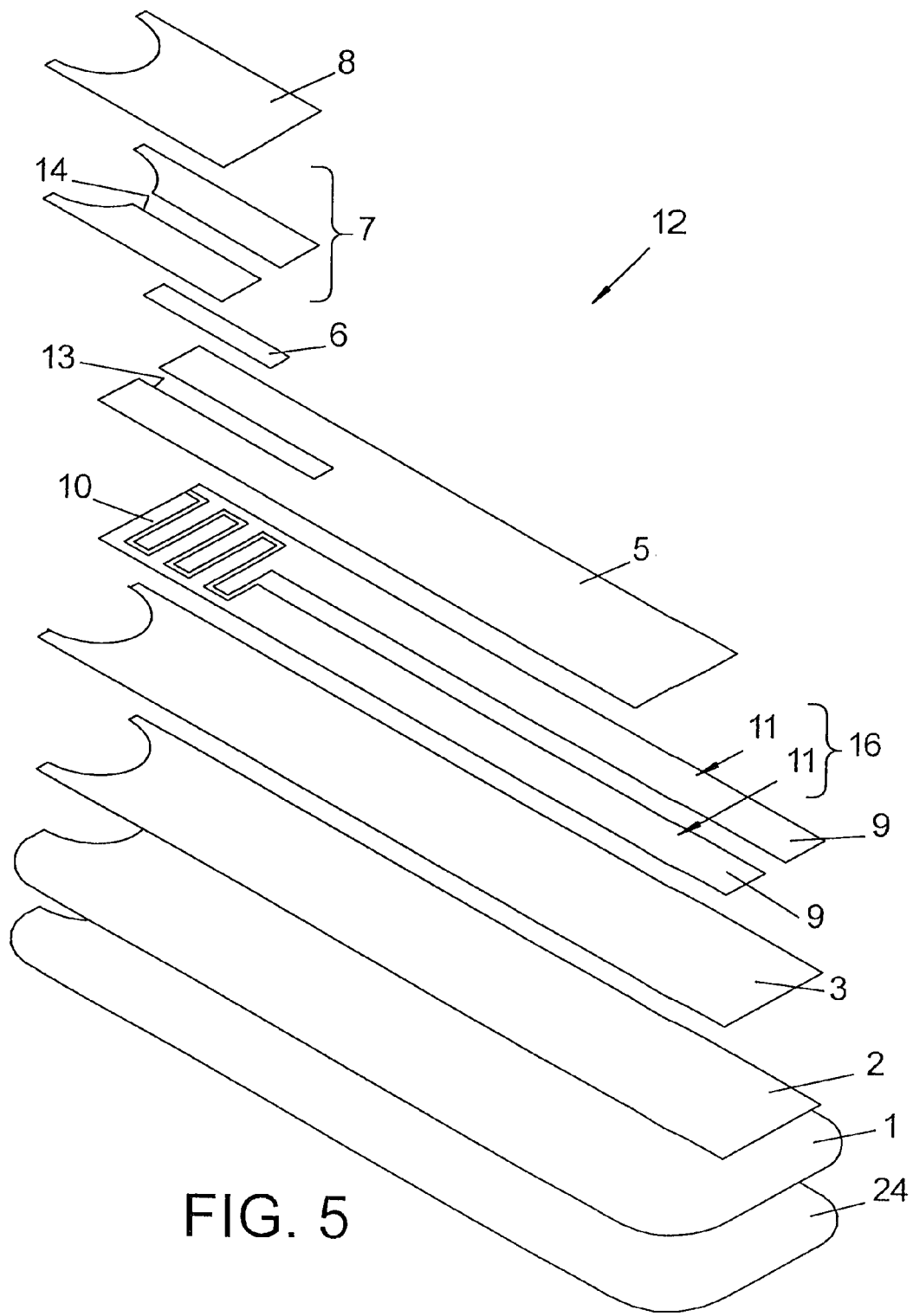
FIG. 5 illustrates an exploded view of another embodiment of a sensor strip of the invention.

FIG. 5 illustrates an exploded view of another embodiment of a sensor strip 12, which includes a base 1 on a heat conducting layer 24, and adhesive foil 2 for holding the base to the electrode substrate 3. The electrode set 16, which is made up of the two electrodes 11 and 11, is on the electrode substrate 3, and is partially covered by a dielectric 5. A cover 8 is attached to one end of the dielectric with adhesive tape 7. A small gap 13 in the dielectric, and a space 14 in the adhesive tape, together with the cover and the electrodes, form a pocket inside of which may be placed reagent 6 used to aid in electrochemically detecting and quantifying an analyte. This pocket can act as a capillary, drawing the fluid to be tested onto the sensing region 10 of the electrodes. Alternatively, the cover may be absent, exposing the sensing region of the electrodes, and the sample may be directly applied onto this region.

Figure 6:
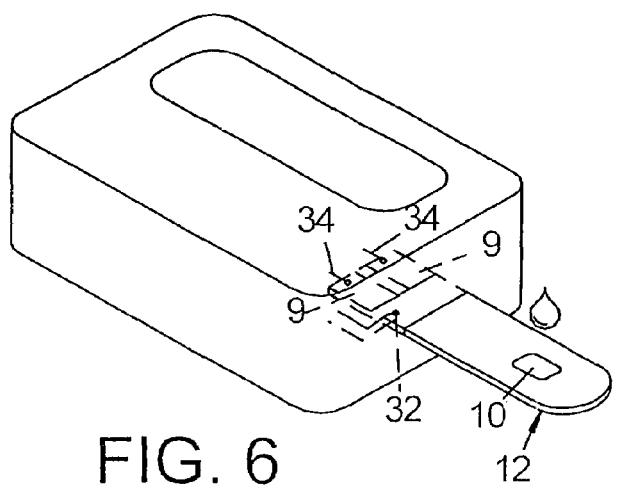
FIG. 6 illustrates a sensor instrument with a sensor strip inserted.

FIG. 6 illustrates a sensor instrument with a sensor strip inserted. As shown, the sensor strip 12 is inserted into the instrument with the end having contact pads 9 and 9 physically inside the instrument. Electrical contacts 34 and 34 make electrical contact with the contact pads. A temperature sensor 32 makes contact with the bottom of the sensor strip, at a surface opposite the contact pads. The temperature sensor is at a side of the gap which receives the sensor strip opposite the electrical contacts. Also shown in the figure is the sensing region 10.

An electrode set includes at least first and second electrodes. The electrodes are separated by a gap that prevents electrical contact between the two electrodes. In FIG. 5, the sensing region of each electrode includes interdigitating fingers. The sensing region is where the actual electrochemical sensing takes place. In the sensing region only a simple straight gap may separate the electodes (as illustrated in FIG. 1), or it may be more complex, for example, containing a rectilinear gap, forming a region of interlacing fingers of the two electrodes.

The length of the electrode set is preferably 2.5 to 250 mm, the width is preferably 0.4 to 40 mm, the gap between the contact pads is preferably 1 μm to 5 mm, and the width of each contact pad is preferably 1 to 20 mm. The electrode pattern is preferably symmetric, however this is not required, and an irregular or asymmetric pattern (or electrode shapes) is possible.

The heat conducting layer improves the overall thermal conductivity of the sensor strip. Without a heat conducting layer, the sensor strip can have a thermal conductivity of 1.41 W/m-K. The heat conducting layer itself has a thermal conductivity of at least 10 W/m-K, preferably of at least 50 W/m-K, more preferably at least 100 W/m-K, and most preferably at least 200 W/m-K. Preferably, the heat conducting layer contains copper, aluminum, which have a thermal conductivity of about 400 and 200 W/m-K, respectively, or alloys of these metals. The heat conducting layer may be a composite material, such as a polymer containing metallic particles or fibers. Furthermore, the heat conducting layer may be coated with one or more material, such as nickel and gold, or a polymer film, to improve its corrosion resistance or appearance. The volume of the heat conducting layer, as based on the total volume of the sensor strip, preferably at least 2%, more preferably at least 5%, even more preferably at least 20%, and most preferably at least 45%. The thickness of the heat conducting layer depends on the thermal conductivity of the heat conducting layer. Preferably the heat conducting layer has a thickness of 0.1 mils to 0.5 inches, more preferably, 0.5 mils to 0.1 inches, most preferably 1 mil to 50 mils.

The heat conducting layer extends at least from an area near the sensing region (but on the opposite side of the electrode substrate) to an area near the contact pads (but on the opposite side of the electrode substrate). Any shape is possible; for example the heat conducting layer may extend the full length and width of the electrode substrate, or it could be a narrow strip which extends from opposite the sensing region to opposite the contact pads. Preferably, the heat conducting layer extends from a first end of the electrode substrate or base (i.e., the end having the contact pads) towards the second end of the substrate or base, to a position in general alignment with the sensing region. It would also be possible for the heat conducting layer to be irregularly shaped, as long as it serves to increase the thermal conductivity of the sensor strip.

The heat conducting layer is not required. Instead it is possible to simply use an electrode substrate that has a thermal conductivity of at least 10 W/m-K, preferably of at least 50 W/m-K, more preferably at least 100 W/m-K, and most preferably at least 200 W/m-K. However, the electrode substrate must be electrically insulating, at least at its surface in order to prevent it from short circuiting the electrodes. Therefore, when a heat conducting layer is not used, the electrode substrate may be made from a highly thermally conductive ceramic, such as diamond, aluminum nitride, or aluminum oxide; or from a composite materials such as a composite of a polymer and metal particles or fibers.

With a heat conducting layer, or with an electrode substrate that has a thermal conductivity of at least 10 W/m-K, the thermal conductivity of the sensor strip is improved. Preferably, the sensor strip has a thermal conductivity of at least 10 W/m-K, more preferably at least 20 W/m-K, even more preferably at least 85 W/m-K, and most preferably at least 190 W/m-K. The thermal conductivity of the sensor strip is the average thermal conductivity as measured from the sensing region to the surface of the sensor strip opposite the contact pads.

The heat conducting layer may be attached to the electrode substrate. Alternatively, if the electrode substrate is attached to a base, the heat conducting layer may be attached to the base. The heat conducting layer may be attached to the electrode substrate or base by an adhesive, an adhesive foil, or directly laminating them together using heat and/or pressure. The heat conducting layer could also be mechanically attached using a clip or fastener. It would also be possible to directly form the heat conducting layer onto the electrode substrate or base, for example, by sputtering or evaporation. Furthermore, it would also be possible to directly form the electrode substrate or base onto the heat conducting layer, for example, by sputtering, evaporation, or polymerizing monomers.

The method of forming of the remainder of the sensor strip is not limited. Any previous method may be used. For example, the electrodes may be formed by sealing foil onto the electrode substrate (for example, gold foil). The electrodes may be screen printed onto the electrode substrate, or a metallic layer may be sputtered and then electrodes formed in it by lithography. Alternatively, the electrodes may be formed by lamination, or laser ablation as described in application Ser. No. 09/411,940, filed Oct. 4, 1999, and entitled "LASER DEFINED FEATURES FOR PATTERNED LAMINATES AND ELECTRODE", hereby incorporated by reference.

Preferably, the electrode includes gold, platinum, palladium, iridium, or alloys of these metals, since such noble metals and their alloys are unreactive in biological systems. The electrodes may be any thickness, but preferably are 10 nm to 1 mm, more preferably, 20 nm to 100 μm, or even 25 nm to 1 μm.

A UV curable dielectric and which is screen printable, may be used to form the dielectric, for example the polymer composition 5018 dielectric composition from DuPont. The clear cover is a clear material that is inert to biological fluids, for example glass, polyethylene, polypropylene, polyvinylchloride, polyimide, or polyester. The clear cover may have markings. The adhesive tape is also a flexible polymer having a surfaces covered with an adhesive; these materials are also well known to those of ordinary skill in the art.

The base is an optional supporting structure, and is preferably made of a flexible polymer material, with a thickness sufficient to provide support to the sensor strip, for example polyester with a thickness of 6 mils. The adhesive foil may be made for the same types of compositions as the adhesive tape.

The reagent is optional, and may be used to provide electrochemical probes for specific analytes. The starting reagents are the reactants or components of the reagent, and are often compounded together in liquid form before application to the ribbons or reels. The liquid may then evaporate, leaving the reagent in solid form. The choice of specific reagent depends on the specific analyte or analytes to be measure, and are well known to those of ordinary skill in the art. For example, a reagent for measurement of glucose in a human blood sample contains 62.2 mg polyethylene oxide (mean molecular weight of 100-900 kilodaltons), 3.3 mg NATROSOL 250 M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase, forming a solution of quinoprotein glucose dehydrogenase. This reagent is described in WO 99/30152, pages 7-10, hereby incorporated by referece.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate butter), and a microcrystalline material (Avicel RC-591F—a blend of 88% microcrystalline cellulose and 12% sodium carboxymethylcellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is incorporated herein by reference.

Other non-limiting examples of enzymes and mediators that may be used in measuring particular analytes in cell 10 of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate Alcohol | Pyruvate Oxidase Alcohol Oxidase | Ferricyanide Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is appreciated that a variety of electrochemical assays may be conducted with cell 10 in accordance with this disclosure.

The sensor strip of the present invention may also include microspheres, as described in pending patent application Ser. No. 09/471,571 entitled "MICROSPHERE CONTAINING SENSOR", inventors Raghbir Singh Bhullar and Brian S. Hill, filed Dec. 23, 1999, hereby incorporated by reference.

The processes and products described include disposable biosensors, especially for use in diagnostic devices. However, also included are electrochemical sensors for non-diagnostic uses, such as measuring an analyte in any biological, environmental, food or other sample. In addition, a plurality of the sensor strips are typically packaged in a vial, usually with a stopper. Furthermore, a new sensor instrument may be used with the sensor strips.

An electrochemical biosensor includes both a sensor strip, as well as a sensor instrument. The sensor strip is inserted into the sensor instrument so that the contact pads mate with electrical contacts in the sensor instrument. The sensor instrument used with the sensor strip of the present invention will also have a temperature sensor, similar to sensor instrument previously known, however, the temperature sensor will be located near the electrical contacts intended to mate with the contact pads, and situated so that the temperature sensor will come into contact with the sensor strip. This will allow the temperature sensor to measure the temperature of the sensor strip itself. Preferably the temperature sensor will be situated so that it will come into contact with the bottom of the sensor strip, more preferably the temperature sensor will come into contact with the heat conducting layer. In all other respects, the sensor instrument of the present invention will be similar to previous sensor instrument, for example the sensor instrument of U.S. Pat. No. 5,405,511, hereby incorporated by reference, except that algorithms intended to determine the temperature of the sample are unnecessary; the temperature measured directly by the temperature sensor may be used as the temperature of the sample. For example, a gap in the sensor instrument, intended to accept the end of the sensor strip having contact pads, will have the electrical contacts for connecting to the contact pads at one end, and an embodiment of the present invention, will have a temperature sensor opposite the electrical contacts.

The invention claimed is:

1. A sensor system for measuring the concentration of an analyte in a biological sample, said sensor system comprising:
   a sensor instrument, said sensor instrument comprising a housing having a gap formed therein, said sensor instrument further comprising electrical contacts at a first side of said gap and a temperature sensor at a second side of said gap opposite said first side; and
   a sensor strip, said sensor strip comprising an electrically-insulating electrode substrate, an electrode set on a first side of said electrode substrate, and a heat conducting layer on a second side of said electrode substrate opposite said first side, said heat conducting layer comprising at least 20% by volume of said sensor strip and having a thermal conductivity of at least 10 W/m-K, said sensor strip receivable in said gap such that said electrode set electrically communicates with said electrical contacts, and said heat conducting layer communicates with said temperature sensor.

2. The sensor system of claim 1, wherein said heat conducting layer comprises a metal or an alloy.

3. The sensor system of claim 2, wherein said metal or. Alloy comprises at least 45% by volume of said sensor strip.

4. The sensor system of claim 1, wherein said sensor strip further comprises a base between said electrode substrate and said heat conducting layer.

5. The sensor system of claim 1, wherein said heat conducting layer has a thermal conductivity of at least 100 W/m-K.

6. The sensor system of claim 1, wherein said heat conducting layer has a thermal conductivity of at least 200 W/m-K.

7. The sensor system of claim 1, wherein said heat conducting layer comprises copper, alloys of copper, aluminum, or alloys of aluminum.

8. The sensor system of claim 7, wherein said heat conducting layer comprises copper.

9. The sensor system of claim 1, wherein said sensor strip further comprises a reagent disposed on said electrode set.

10. The sensor system of claim 9, wherein said reagent comprises at least one agent catalytically reactive with said analyte for electrochemically measuring said analyte concentration.

11. The sensor system of claim 10, wherein said sensor strip further comprises a dielectric disposed on said electrode set.

12. The sensor system of claim 10, wherein the analyte is glucose, and the reagent comprises glucose dehydrogenase.

13. The sensor system of claim 10, wherein the analyte is glucose, and the reagent comprises glucose dehydrogenase and ferricyanide.

14. The sensor system of claim 10, wherein the analyte is glucose, and the reagent comprises glucose dehydrogenase and diaphorase.

15. A method for measuring the concentration of an analyte in a sample, comprising:
   providing an electrochemical sensor system, said electrochemical sensor system comprising a sensor instrument and a sensor strip, said sensor instrument comprising a housing having a gap formed therein for receiving said sensor strip, electrical contacts at a first side of said gap, and a temperature sensor at a second side of said gap; said sensor strip comprising an electrically-insulating electrode substrate, an electrode set on a first side of said electrode substrate, and a conducting portion on a second side of said electrode substrate, said conducting portion comprising at least 20% by volume of said sensor strip and having a thermal conductivity of at least 10 W/m-K, said electrode set comprising at least two electrodes, said sensor strip further comprising a sensing region for receiving said sample;
   inserting said sensor strip into said sensor instrument gap such that said electrodes electrically communicate with said electrical contacts, and said conducting portion thermally communicates with said temperature sensor;
   applying said sample to said sensing region of said sensing strip; and
   electrochemically reacting said analyte in said sample with a reagent to provide an electrochemical signal corresponding to a concentration of the analyte in the sample at a temperature of said conducting portion.

16. The method of claim 15, wherein said electrical contacts are at an upper side of said gap, and said temperature sensor is at a lower side of said gap, and wherein said temperature sensor contacts a bottom portion of said sensor strip.

17. The method of claim 16, wherein said bottom portion of said sensor strip comprises a heat conducting layer.

18. The method of claim 17, wherein said heat conducting layer comprises at least one copper, alloys of copper, aluminum, or alloys of aluminum.

19. The method of claim 17, wherein said heat conducting layer comprises copper.

* * * * *